United States Patent
Gillberg (10) Patent No.: US 7,559,900 B2
(45) Date of Patent: Jul. 14, 2009

(54) CARDIAC SENSING AND DETECTION USING SUBCUTANEOUS ECG SIGNALS AND HEART SOUNDS

(75) Inventor: Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 18 days.

(21) Appl. No.: 11/112,072

(22) Filed: Apr. 22, 2005

(65) Prior Publication Data
US 2006/0241702 A1 Oct. 26, 2006

(51) Int. Cl.
*A61B 5/04* (2006.01)
(52) U.S. Cl. .................. 600/508; 381/67; 600/514
(58) Field of Classification Search ........... 600/508, 600/515, 513, 514; 607/36, 115; 381/67
See application file for complete search history.

(56) References Cited

U.S. PATENT DOCUMENTS

| | | | |
|---|---|---|---|
| 5,331,966 A | 7/1994 | Bennett et al. | 128/696 |
| 5,836,987 A | 11/1998 | Baumann et al. | 607/17 |
| 6,174,278 B1 | 1/2001 | Jaeger et al. | 600/23 |
| 6,198,952 B1 | 3/2001 | Miesel | 600/339 |
| 6,400,982 B2 * | 6/2002 | Sweeney et al. | 600/515 |
| 6,409,675 B1 | 6/2002 | Turcott | 600/508 |
| 6,440,082 B1 | 8/2002 | Joo et al. | 600/528 |
| 6,477,406 B1 * | 11/2002 | Turcott | 600/518 |
| 6,527,729 B1 | 3/2003 | Turcott | 600/528 |
| 6,752,765 B1 | 6/2004 | Jensen et al. | 600/536 |
| 6,869,404 B2 | 3/2005 | Schulhauser et al. | 600/528 |
| 2002/0151938 A1 | 10/2002 | Cobucci | 607/25 |
| 2003/0105497 A1 | 6/2003 | Zhu et al. | 607/17 |
| 2004/0167416 A1 | 8/2004 | Lee | 600/513 |
| 2004/0220460 A1 | 11/2004 | Roberts | 600/333 |
| 2004/0230129 A1 | 11/2004 | Haefner | |
| 2004/0230229 A1 | 11/2004 | Lovett et al. | |

* cited by examiner

*Primary Examiner*—Carl H Layno
*Assistant Examiner*—Brian T Gedeon
(74) *Attorney, Agent, or Firm*—Michael C Soldner (57) ABSTRACT

A method and device for detecting cardiac signals that includes a first plurality of electrodes that senses cardiac signals and delivers therapy, and a second plurality of electrodes that senses the cardiac signals. A microprocessor detects a cardiac event in response to the sensing by the first plurality of electrodes, and verifies the cardiac event in response to the sensing by the second plurality of electrodes.

24 Claims, 8 Drawing Sheets

CARDIAC SENSING AND DETECTION USING SUBCUTANEOUS ECG SIGNALS AND HEART SOUNDS

FIELD OF THE INVENTION

The present invention relates generally to medical devices, and, more particularly, to a method and apparatus for sensing and detecting cardiac signals in a medical device.

BACKGROUND OF THE INVENTION

Implantable medical devices (IMDs) have many functions including the delivery of therapies to cardiac patients, neurostimulators, muscular stimulators, and so forth. For purposes of this application reference will be made only to implantable cardiac devices, it being understood that the principles herein may have applicability to other implantable medical devices as well.

An implantable cardiac device (ICD) may be a device commonly referred to as a pacemaker, which is used to stimulate the heart into a contraction if the sinus node of the heart is not properly timing, or pacing, the contractions of the heart. Modern cardiac devices also perform many other functions beyond that of pacing. For example, some cardiac devices may also perform therapies such as defibrillation and cardioversion as well as providing several different pacing therapies, depending upon the needs of the user and the physiologic condition of the user's heart. For convenience, all types of implantable cardiac devices will be referred to herein as ICDs, it being understood that the term, unless otherwise indicated, is inclusive of an implantable device capable of administering any of a number of therapies to the heart of the user.

In typical use, an ICD is implanted in a convenient location usually under the skin of the user and in the vicinity of the one or more major arteries or veins. One or more electrical leads connected to the pacemaker are inserted into or on the heart of the user, usually through a convenient vein or artery. The ends of the leads are placed in contact with the walls or surface of one or more chambers of the heart, depending upon the particular therapies deemed appropriate for the user.

One or more of the leads is adapted to carry a current from the pacemaker to the heart tissue to stimulate the heart in one of several ways, again depending upon the particular therapy being delivered. The leads are simultaneously used for sensing the physiologic signals provided by the heart to determine when to deliver a therapeutic pulse to the heart, and the nature of the pulse, e.g., a pacing pulse or a defibrillation shock.

There has been recent interest in development of implantable defibrillators that may be inserted entirely subcutaneously or sub-muscularly, having no leads or electrodes positioned within the thoracic cavity. The elimination of transvenous or epicardial leads is believed likely to allow for implant of the devices by a wider range of physicians, in some cases at a lower cost than traditional ICDs. Absence of transvene or epicardial leads may reduce acute and long term complications. Such devices, are therefore believed to offer the opportunity for increased levels of use, particularly for prophylactic implant. US Application Publication Nos. 2002/0042634, 200200068958 and 2002/0035377 to Bardy et al., are exemplary of current thinking with regard to such subcutaneous ICDs. Additional subcutaneous ICDs are disclosed in US Application Publication No. 20020082658 by Heinrich et al. and PCT publication WO/04043919A2 by Olson. All of the above cited applications and publications are incorporated herein by reference in their entireties.

One potential problem associated with the sensing of the physiologic signal from the heart in both the transvenous systems and the subcutaneous systems relates to what is often referred to as "false positive" and "false negative" detections. The most widely accepted detection algorithm is based on the rate of depolarizations of the ventricles, or simply on "heart rate". Such algorithms rely on detecting events based upon signals obtained between two electrodes positioned within or on the heart. If the number of detected events per a given time is greater than a preset value, then the device charges an energy storage capacitor and then shocks the heart; otherwise no shock is delivered. However, cutaneous and subcutaneous ECG signals can sometimes be corrupted by muscle noise and/or other artifacts, such as baseline wander, for example, making reliable R-wave sensing problematic. Accordingly, what is needed is a method and apparatus for improving detection of arrhythmias in a medical device.

BRIEF DESCRIPTION OF THE DRAWINGS

Aspects and features of the present invention will be readily appreciated as they become better understood by reference to the following detailed description when considered in connection with the accompanying drawings, wherein.

DETAILED DESCRIPTION OF THE INVENTION

Figure 1:
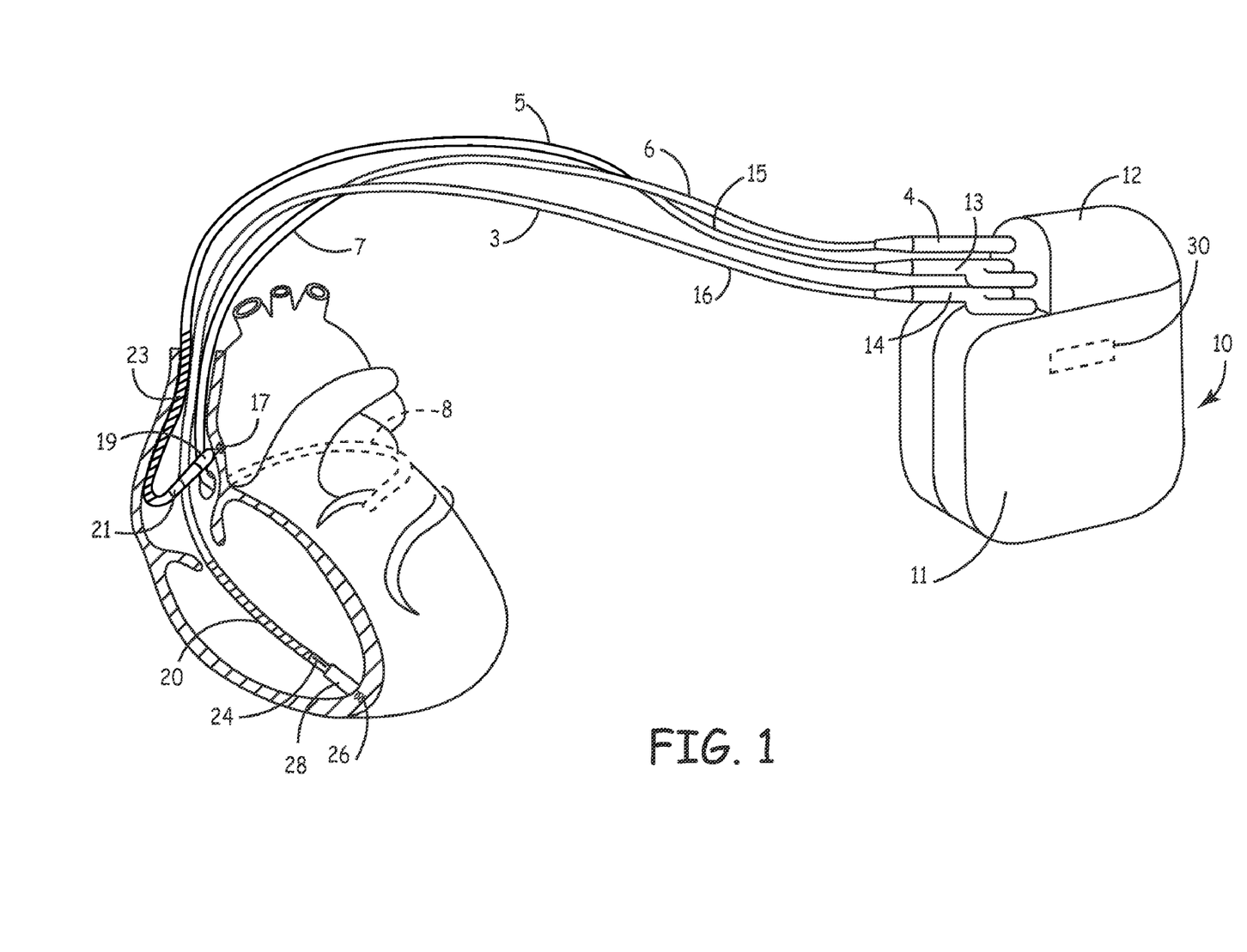
FIG. 1 is a schematic diagram of a an exemplary medical device of a type in which the present invention may usefully be practiced.

FIG. 1 is a schematic diagram of an exemplary medical device of a type in which the present invention may usefully be practiced. As illustrated in FIG. 1, an exemplary medical device 10 according to an embodiment of the present invention includes a ventricular lead 3, an atrial/SVC lead 5 and a coronary sinus lead 7 coupled to a device housing 11 via a connector block 12 positioned along housing 11. Ventricular lead 3 includes an elongated insulative lead body 16, carrying three mutually insulated conductors. Located adjacent the distal end of lead 3 are a ring electrode 24, an extendable helix electrode 26, mounted retractably within an insulative electrode head 28, and an elongated coil electrode 20. Each of electrodes 24-28 is coupled to one of the conductors (not shown) within the lead body 16. Electrodes 24 and 26 are employed for cardiac pacing and for sensing ventricular depolarizations. A bifurcated connector 14 at the proximal end of lead 3 carries electrical connectors coupled to the coiled conductors.

Atrial/SVC lead 5 includes an elongated insulative lead body 15, also carrying three mutually insulated conductors (not shown). Located adjacent the J-shaped distal end of the lead are a ring electrode 21 and an extendible helix electrode 17, mounted retractably within an insulative electrode head 19. Each of electrodes 17 and 21 is coupled to one of the conductors within the lead body 15. Electrodes 17 and 21 are employed for atrial pacing and for sensing atrial depolarizations. An elongated coil electrode 23 is provided, proximal to electrode 21 and coupled to the third conductor within the lead body 15. A bifurcated connector 13 is positioned at the proximal end of lead 5 and includes three electrical connectors, each coupled to one of the coiled conductors, to connect the conductors to circuitry within housing 11 of device 10.

Coronary sinus lead 7 includes an elongated insulative lead body 6, carrying one conductor, coupled to an elongated coiled defibrillation electrode 8. Electrode 8, illustrated in broken outline, is located within the coronary sinus and great vein of the heart. At the proximal end of the lead is a connector plug 4, which carries an electrical connector, coupled to the coiled conductor.

According to an embodiment of the present invention, medical device 10 of FIG. 1 is a pacemaker/cardioverter/defibrillator having electronic circuitry used for generating cardiac pacing pulses for delivering cardioversion and defibrillation shocks and for monitoring the patient's heart rhythm located within housing 11. Medical device 10 is shown with the lead connector assemblies 4, 13 and 14 inserted within connector block 12, which serves as a receptacle and electrical connector for receiving connectors 4, 13 and 14 and interconnecting the leads to the circuitry within housing 11. As will be described in more detail, medical device 10 includes one or more secondary sensors that are utilized during detection of cardiac rhythms. The sensor or sensors may either be positioned along a lead or a device housing, such as along a header block of the medical device 10, or, as illustrated schematically in FIG. 1 by broken outline, a secondary sensor 30 is positioned along housing 11 of medical device 10, for example. According to the present invention, the secondary sensor(s) are used for verifying detection of cardiac rhythms, as will be described in detail below.

Optionally, device may include an uninsulated portion of housing 11 that serves as a subcutaneous defibrillation electrode, used to defibrillate either the atria or ventricles. Other lead configurations and electrode locations may of course be substituted for the lead set illustrated. For example, atrial defibrillation and sensing electrodes might be added to either the coronary sinus lead or the right ventricular lead instead of being located on a separate atrial lead, allowing for a two-lead system.

Figure 2:
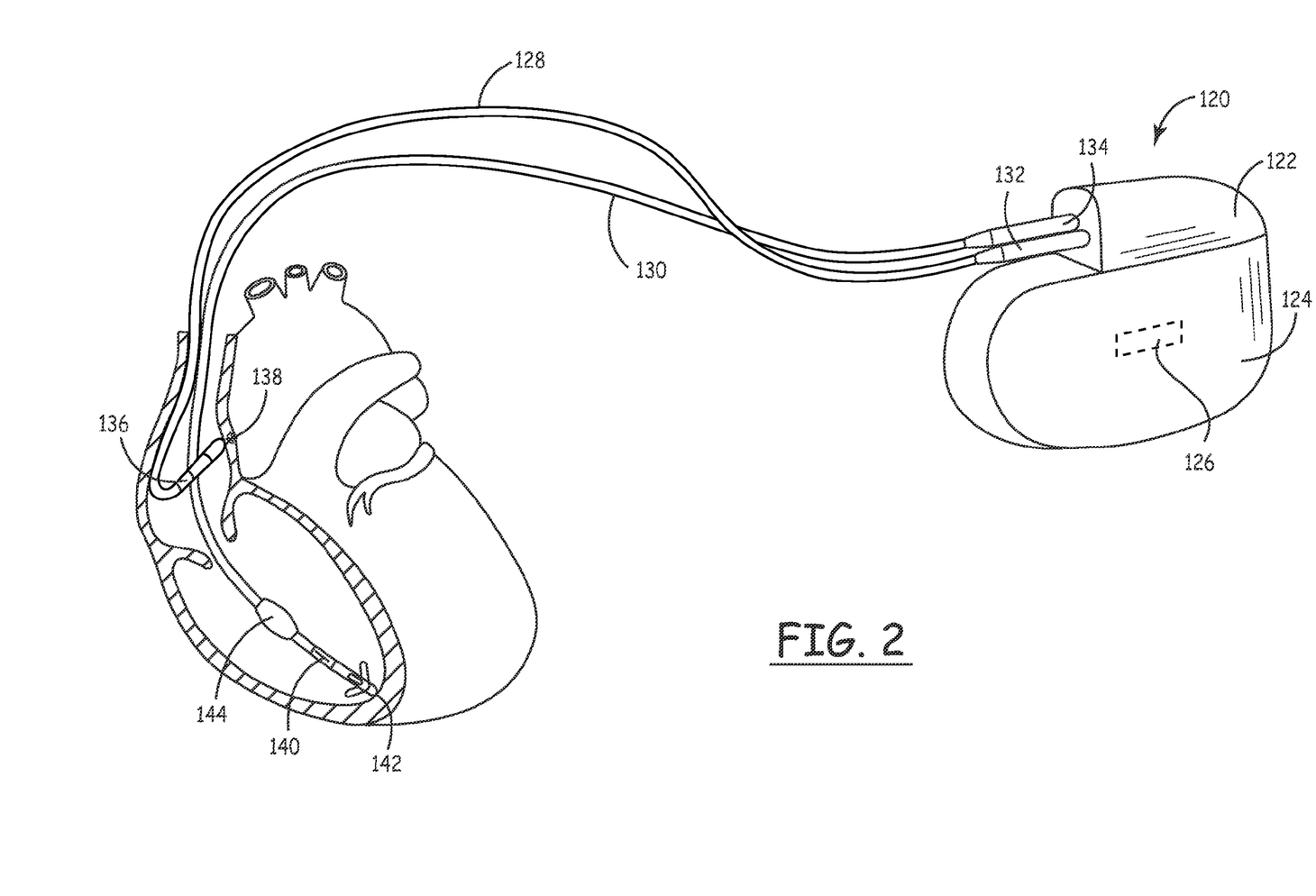
FIG. 2 is a schematic diagram of an exemplary medical device of a type in which the present invention may usefully be practiced.

FIG. 2 is a schematic diagram of an exemplary medical device of a type in which the present invention may usefully be practiced. As illustrated in FIG. 2, an exemplary medical device 120 according to an embodiment of the present invention may be a cardiac pacemaker that includes a hermetically sealed housing 124 containing the electronic circuitry used for generating cardiac pacing pulses and for monitoring the patient's heart rhythm. Mounted to housing 124 is a header 122 which serves as a receptacle and electrical connector for receiving the connectors 132 and 134 of pacing leads 128 and 130 and interconnecting the leads to the circuitry within housing 124. Lead 128 is a ventricular lead provided with electrodes 140 and 142 for monitoring right ventricular heart signals. Atrial lead 130 carries electrodes 136 and 138 and is employed for sensing and pacing the patient's atrium.

Medical device 120 includes one or more secondary sensors positioned along either one of leads 128, 130 or along housing 124 or header 122, or along any combination of the lead, housing 124, or header 122, as described above. The device 120 of FIG. 2 is shown having a secondary sensor 126 illustrated schematically by broken outline along housing 124 and a secondary sensor 144 positioned along lead 128. Sensor 144 may be used in conjunction with or as an alternative to sensor 126 for verifying the detection of cardiac rhythms, as described below.

Figure 3:
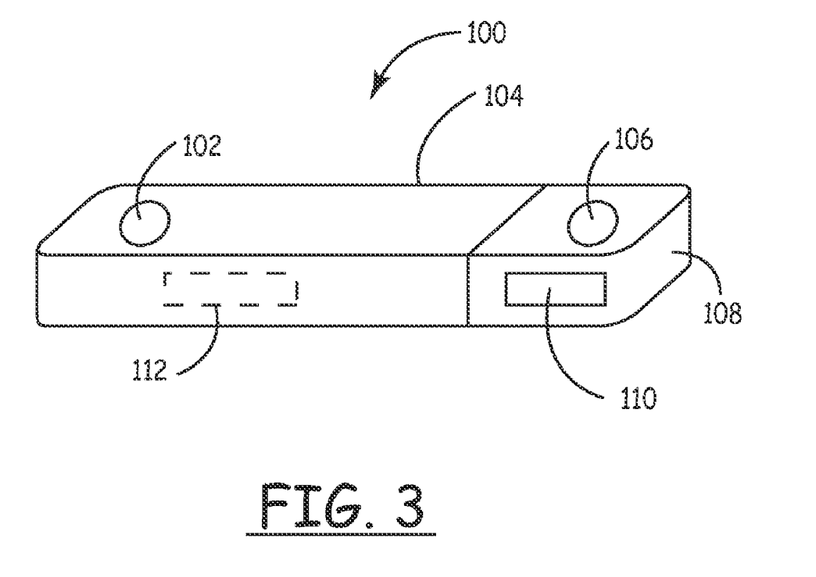
FIG. 3 is a schematic diagram of an exemplary medical device of a type in which the present invention may usefully be practiced.

FIG. 3 is a schematic diagram of an exemplary medical device of a type in which the present invention may usefully be practiced. As illustrated in FIG. 3 an exemplary medical device 100 according to an embodiment of the present invention may be a subcutaneously implantable monitor that includes a hermetically sealed housing 104 containing the electronic circuitry used for generating cardiac pacing pulses and for monitoring the patient's heart rhythm and which carries a molded plastic header 108. Housing 104 and header 108 each carry an electrode 102 and 106, respectively for monitoring heart rhythm. Also mounted in the header 108 is an antenna 110 for use in communicating between the device and an external programmer. Medical device 100 includes one or more secondary sensors positioned along housing 104 that may be used to verify detection of cardiac rhythms, as described below. Medical device 100 is shown in FIG. 3, for example, as having a sensor 112, illustrated in broken outline, positioned along housing 104. Signals are detected between the electrodes 102 and 106 and normal detection algorithms are utilized, with signals detected by secondary sensor 112 being utilized to verify detected cardiac rhythms, as will be described below.

Figure 4:
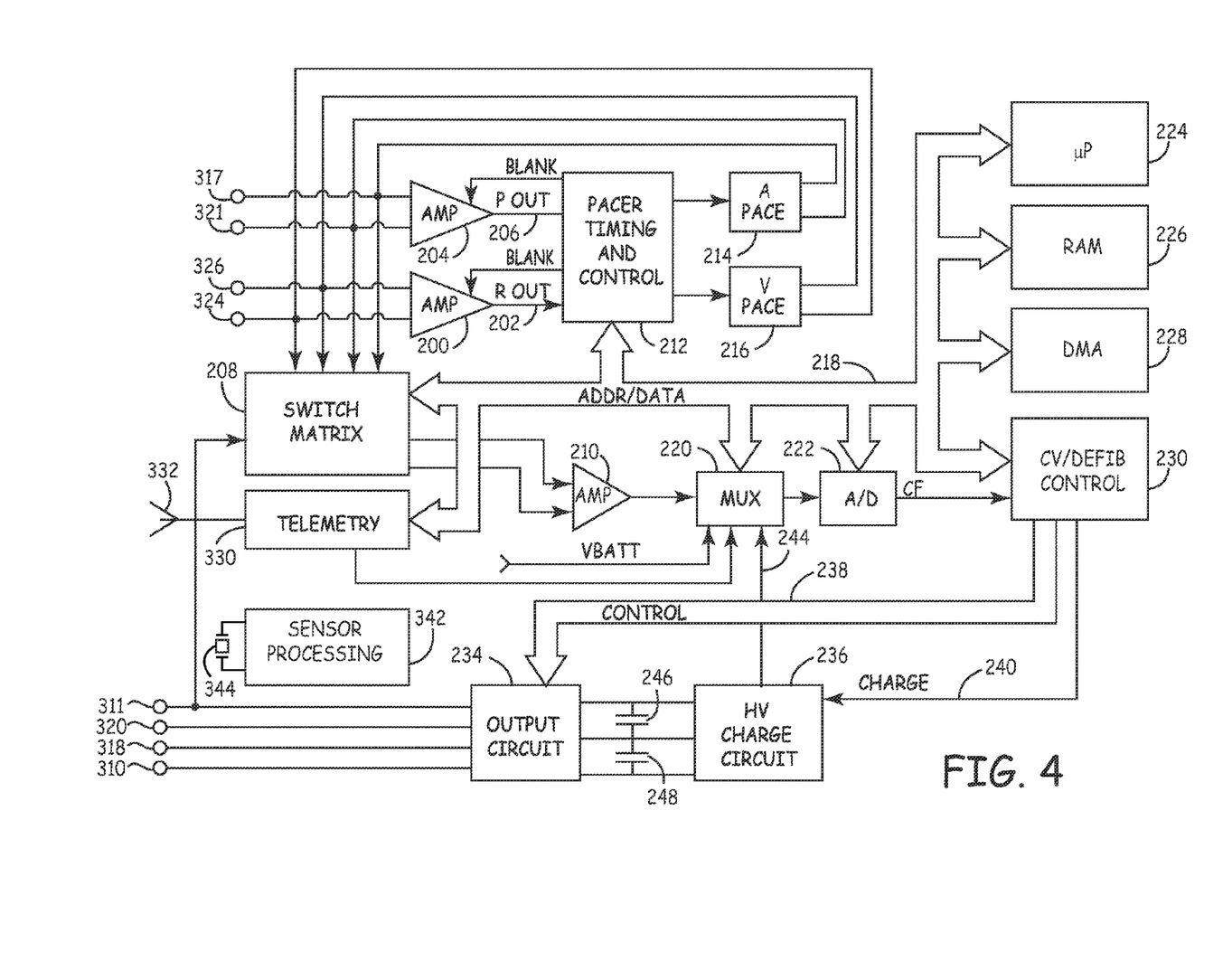
FIG. 4 is a functional schematic diagram of the medical device of FIG. 1, in which the present invention may usefully be practiced.

FIG. 4 is a functional schematic diagram of the medical device of FIG. 1, in which the present invention may usefully be practiced. This diagram should be taken as exemplary of one type of anti-tachyarrhythmia device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to the electrode associated with the uninsulated portion of the housing 11 of the medical device that serves as a defibrillation electrode. Electrode 320 corresponds to electrode 20 and is a defibrillation electrode located in the right ventricle. Electrode 310 corresponds to electrode 8 and is a defibrillation electrode located in the coronary sinus. Electrode 318 corresponds to electrode 23 and is a defibrillation electrode located in the superior vena cava. Electrodes 324 and 326 correspond to electrodes 24 and 26, and are used for sensing and pacing in the ventricle. Electrodes 317 and 321 correspond to electrodes 19 and 21 and are used for pacing and sensing in the atrium. Finally, sensor 344 corresponds to the secondary sensor or sensors 30 positioned along housing 11 and/or a lead included with the device.

Electrodes 310, 311, 318 and 320 are coupled to high voltage output circuit 234. Electrodes 324 and 326 are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are coupled to the P-wave amplifier 204, which preferably also takes the form of an automatic gain controlled amplifier providing an adjustable sensing threshold as a function of the measured R-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824 to Keimel, et al., incorporated herein by reference in its entirety. However, any of the numerous prior art sense amplifiers employed in implantable cardiac pacemakers, defibrillators and monitors may also usefully be employed in conjunction with the present invention. Switch matrix 208 is used to select which of the available electrodes are coupled to wide band amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal-processing methodologies known to the art.

Telemetry circuit 330 receives downlink telemetry from and sends uplink telemetry to the patient activator by means of antenna 332. Data to be uplinked to the activator and control signals for the telemetry circuit are provided by microprocessor 224 via address/data bus 218. Received telemetry is provided to microprocessor 224 via multiplexer 220. The atrial and ventricular sense amp circuits 200, 204 produce atrial and ventricular EGM signals, which also may be digitized, and uplink telemetered to an associated programmer on receipt of a suitable interrogation command. The device may also be capable of generating so-called marker codes indicative of different cardiac events that it detects. A pacemaker with marker-channel capability is described, for example, in U.S. Pat. No. 4,374,382 to Markowitz, which patent is hereby incorporated by reference herein in its entirety. The particular telemetry system employed is not critical to practicing the invention, and any of the numerous types of telemetry systems known for use in implantable devices may be used. In particular, the telemetry systems as disclosed in U.S. Pat. No. 5,292,343 issued to Blanchette et al., U.S. Pat. No. 5,314,450, issued to Thompson, U.S. Pat. No. 5,354,319, issued to Wybomy et al. U.S. Pat. No. 5,383,909, issued to Keimel, U.S. Pat. No. 5,168,871, issued to Grevious, U.S. Pat. No. 5,107,833 issued to Barsness or U.S. Pat. No. 5,324,315, issued to Grevious, all incorporated herein by reference in their entireties, are suitable for use in conjunction with the present invention. However, the telemetry systems disclosed in the various other patents cited herein which are directed to programmable implanted devices, or similar systems may also be substituted. The telemetry circuit 330 is of course also employed for communication to and from an external programmer, as is conventional in implantable anti-arrhythmia devices.

Signals detected by the one or more secondary sensors 344 are processed by sensor processing circuitry 342 and utilized by microprocessor 224 to verify detection of cardiac rhythms, as will be described below. In addition, while the present invention may be utilized in a device that does not including pacing therapy, in those devices in which pacing is included, sensors 344 and circuitry 342 may be employed in the conventional fashion described in U.S. Pat. No. 4,428,378 issued to Anderson et al, incorporated herein by reference in its entirety, to regulate the underlying pacing rate of the device in rate responsive pacing modes in addition to functioning as a secondary sensor for verifying the detection of cardiac rhythms.

The remainder of the circuitry is dedicated to the provision of cardiac pacing, cardioversion and defibrillation therapies, and, for purposes of the present invention may correspond to circuitry known in the prior art. An exemplary apparatus is disclosed for accomplishing pacing, cardioversion and defibrillation functions as follows, although other embodiments may not include pacing. The pacer timing/control circuitry 212 includes programmable digital counters which control the basic time intervals associated with DDD, WI, DVI, VDD, AAI, DDI, DDDR, WIR, DVIR, VDDR, AAIR, DDIR and other modes of single and dual chamber pacing well known to the art. Circuitry 212 also controls escape intervals associated with anti-tachyarrhythmia pacing in both the atrium and the ventricle, employing, any anti-tachyarrhythmia pacing therapies known to the art.

Intervals defined by pacing circuitry 212 may include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including anti-tachyarrhythmia pacing.

The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, PR intervals and R-P intervals, which measurements are stored in memory 226.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. Microprocessor 224 includes associated ROM in which the stored program controlling its operation as described below resides. A portion of the memory 226 may be configured as a plurality of re-circulating buffers, capable of holding series of measured intervals, which may be analyzed in response to the occurrence of a pace or sense interrupt to determine whether the patient's heart is presently exhibiting atrial or ventricular tachyarrhythmia.

The cardiac rhythm detection method of the present invention may include any of the numerous available prior art tachyarrhythmia detection algorithms. One preferred embodiment may employ all or a subset of the rule-based detection methods described in U.S. Pat. No. 5,545,186 issued to Olson et al. or in U.S. Pat. No. 5,755,736 issued to Gillberg et al., both incorporated herein by reference in their entireties. However, any of the various other arrhythmia detection methodologies known to the art might also be utilized.

In the event that an atrial or ventricular tachyarrhythmia is detected, and an anti-tachyarrhythmia pacing regimen is desired, timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization. In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse.

Figure 5:
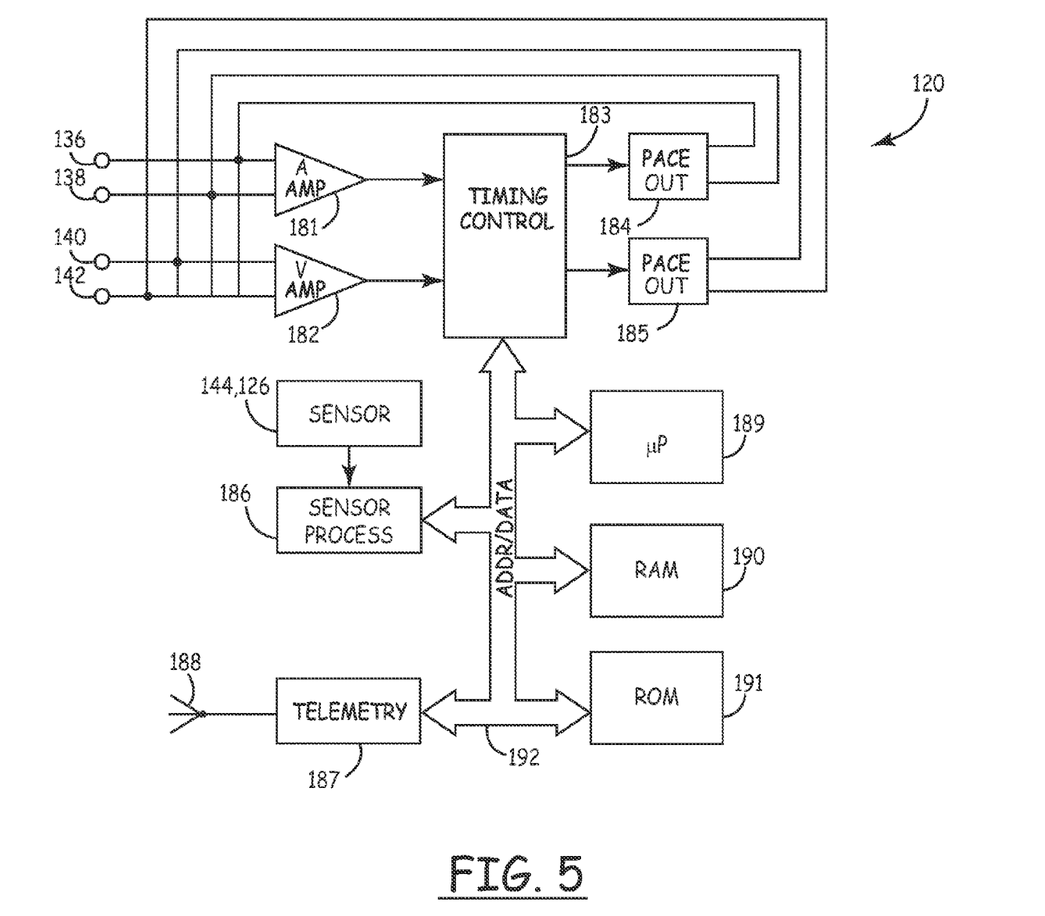
FIG. 5 is a functional schematic diagram of the medical device of FIG. 2 according to an embodiment of the present invention.

FIG. 5 is a functional schematic diagram of the medical device of FIG. 2. The medical device of FIGS. 2 and 5 is essentially a set of subcomponents of the medical device illustrated in FIGS. 1 and 4. Like the medical device of FIG. 4, the medical device of FIG. 5 is a microprocessor-controlled device with microprocessor 189 operating under control of programming stored in Read Only Memory (ROM) 191. In the device as illustrated, electrodes 136 and 138, intended for location in the atrium of the patient's heart are coupled to an atrial amplifier 181 which may correspond to atrial amplifier 204 in FIG. 4. Similarly, ventricular electrodes 140 and 142 are coupled to ventricular amplifier 182, which may correspond to ventricular amplifier 200 in FIG. 4. The outputs of atrial and ventricular amplifiers 181 and 182 are input into timing and control circuitry 183 which conforms generally to the pacer timing and control circuitry 212 of FIG. 4, and which measures intervals between detected depolarizations and controls intervals between delivered pacing pulses as well as generating interrupts via data/address 192 to awake microprocessor 189 in response to delivery of a pacing pulse or sensing of a cardiac depolarization. Intervals between depolarizations measured by timing/control circuitry 183 are stored in Random Access Memory (RAM) 190 until processed by microprocessor 189 to derive average heart rate values. Atrial and ventricular pacing pulses delivered according to one or more of the standard pacing modes described in conjunction with FIG. 4 are produced by atrial and ventricular pulse generator circuits 184 and 185 which may correspond to pulse generator circuits 215 and 216 in FIG. 4.

As described above, signals detected by the one or more secondary sensors 144, 126 are processed by sensor processing circuitry 186 and utilized by microprocessor 189 to verify detection of cardiac rhythms, as will be described below. In addition, sensors 144, 126 and circuitry 186 may be employed in the conventional fashion described in U.S. Pat. No. 4,428,378 issued to Anderson et al, incorporated herein by reference in its entirety, to regulate the underlying pacing rate of the device in rate responsive pacing modes and also serves as a secondary sensor for verifying the detection of an arrhythmia.

Figure 6:
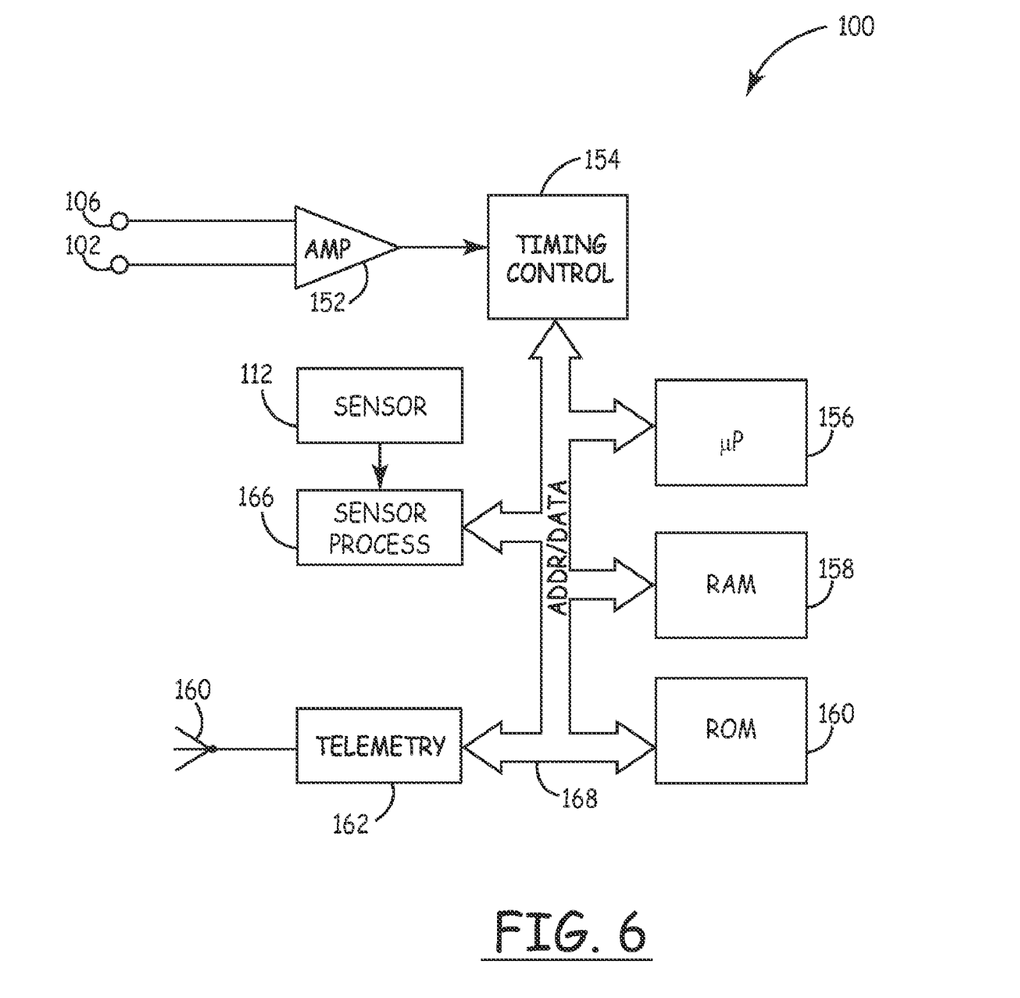
FIG. 6 is a functional schematic diagram of the medical device of FIG. 3 according to an embodiment of the present invention.

FIG. 6 is a functional schematic diagram of the medical device of FIG. 3. As illustrated in FIG. 6, device 100 consists essentially of a set of subcomponents of the more complex embodiment of the invention disclosed in FIGS. 4 and 5, and includes a sense amplifier 152 coupled to electrodes 102 and 106, illustrated in FIG. 3. Sense amplifier 152 may correspond to sense amplifier 204 or 200 in FIG. 5. Like the device of FIGS. 4 and 5, medical device 100 may be a microprocessor control device operating under control microprocessor 156 with its functionality controlled primarily by software stored in the read only memory associated therein. In this context, amplifier 152 detects the occurrence of heart depolarizations, with timing/control circuitry 154 serving to measure the durations between the detected heart depolarizations and to generate interrupts awakening microprocessor 156 so that it may store, analyze and process the detected intervals. Random Access Memory (RAM) 158 serves to store measured and calculated parameters including the calculated average heart rate values for later telemetry to an external device. Like the device in FIGS. 4 and 5, timing and control circuitry communicates with the microprocessor and the remaining circuitry by means of the address/data bus 168. Telemetry system 162 may correspond to telemetry system 330 in FIG. 4, with antenna 110 transmitting and receiving information from the external programmer, including information stored in RAM 158.

As described above, signals detected by the one or more secondary sensors 112 are processed by sensor processing circuitry 166, which may correspond to sensor processing circuitry 342 in FIG. 4, and utilized by microprocessor 224 to verify detection of cardiac rhythms, as will be described below.

Figure 7:
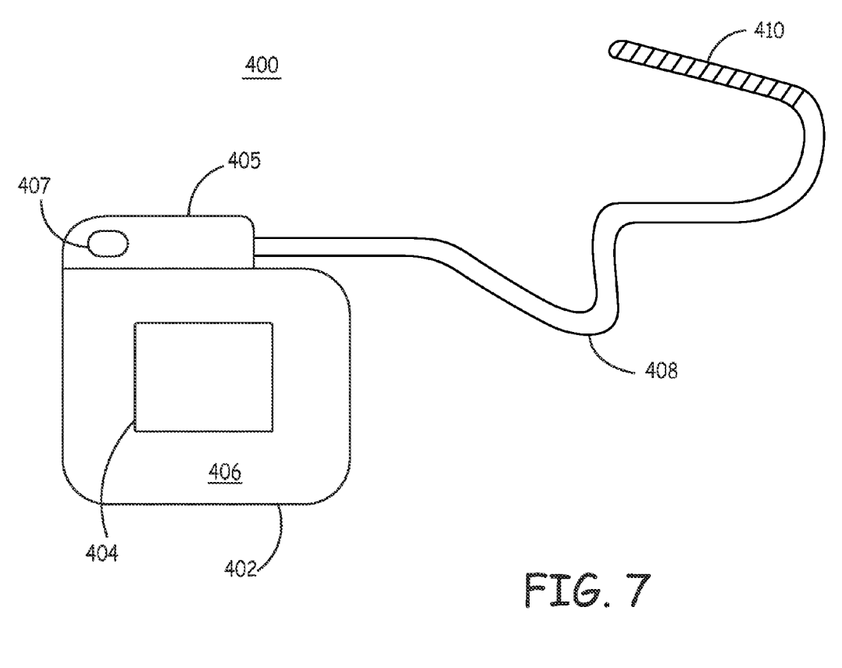
FIG. 7 is a schematic diagram of an exemplary medical device according to an embodiment of the present invention.

FIG. 7 is a schematic diagram of an exemplary medical device according to an embodiment of the present invention. As illustrated in FIG. 7, a medical device 400 in which the present invention may be usefully practiced may include a subcutaneous cardioverter/defibrillator, for example. Such a medical device 400 includes a housing 402 having an electrode 404 positioned along a side wall 406 of housing 402 that is to be positioned subcutaneously within the patient. A header 405 of housing 402 is coupled to a subcutaneous lead 408 carrying conventional conductors (not shown) extending therethrough to electrically couple circuitry located within housing 402 to an electrode 410 positioned distally on the lead 408. The housing 402 and the lead 408 are positioned subcutaneously within the patient so that electrodes 404 and 410 are directed towards the patient's heart. In particular, according to an embodiment of the present invention, the lead 408 extends posteriorly around the patient's back and the housing 402 is subcutaneously implanted outside the patient's ribcage anterior to the cardiac notch, for example, to provide a desired defibrillation vector. Sensing may be performed between electrodes 404 and 410, or between electrode 404 on the housing 402 and a ring electrode positioned along the lead 408 distally from electrode 410. Sensing may also be accomplished using two electrodes positioned along the housing 402.

As illustrated in FIG. 7, medical device 400 includes one or more secondary sensors 407 in combination with any desired number of sensing and/or therapy delivering electrodes, positioned either along lead 408, housing 402, or header 405, or along any combination of lead 408, housing 402 and header 405. As illustrated in FIG. 7, secondary sensor 407 is positioned along header 407 of housing 402, although, although other locations may also be utilized for the one or more secondary sensors, such as being positioned along lead 408 or along a separate patch coupled to housing 402 via a separate subcutaneous lead. Secondary sensor(s) may be used in conjunction with or as an alternative to sensor 404 and 410 for verifying the detection of cardiac rhythms, as described below.

Other subcutaneous cardioverter/defibrillator medical devices in which the present invention may be usefully practiced may include, for example, the devices described in commonly assigned U.S. patent application Ser. No. 11/004, 498, entitled "Subcutaneous Implantable Cardioverter/ Defibrillator, by Ghanem et al., Dec. 3, 2004, or commonly assigned U.S. patent application Ser. No. 11/037,123, entitled "Method and Apparatus for Detection in a Medical Device", by Mitrani et al. and filed Jan. 18, 2005, both incorporated herein by reference in their entireties.

According to an embodiment of the present invention, the secondary sensor or sensors may correspond to an acoustic sensor, formed, for example, from a piezoelectric material, which may be a piezoelectric ceramic, film, or polymer. In an alternative embodiment, heart sound sensor may be provided as a miniaturized microphone. However, a piezoelectric material does not require an energizing power supply, allowing the battery size required by the medical device to be minimized, reducing the overall size of the device. As described above, the sensor or sensors may be positioned on or within the housing of the medical device, and electrically coupled to a circuit board within device housing, or positioned along one or more leads, or positioned within a header block on the device housing. The sensors are preferably hermetically sealed against body fluids, and mounted on a diaphragm or other component that stabilizes the position of sensor 22 while providing good acoustical coupling. A monitor housing including a microphone diaphragm, for example, which may be adapted for use with the present invention, is generally disclosed in U.S. Pat. No. 6,409,675, issued to Turcott, incorporated herein by reference in its entirety.

The sensor or sensors may be provided as a hard piezoelectric ceramic, a relatively soft piezoelectric ceramic, or a flexible piezoelectric film formed from a piezoelectric polymer such as polyvinylidene fluoride. For example, a soft piezoelectric ceramic such as Model PZT-5A available from Morgan Electro Ceramics, may utilized.

In addition, the sensor or sensors may correspond to an activity sensor, a respiration sensor, for example as disclosed in U.S. Pat. No. 5,562,711 issued to Yerich et al or a hemodynamic sensor 140, a hemodynamic sensor, such as an oxygen saturation sensor in conjunction with associated processing circuitry as described in U.S. Pat. No. 5,903,701 issued to Moore or U.S. Pat. No. 6,198,952 issued to Miesel, a pressure or temperature sensor and associated sensor processing circuitry as described in U.S. Pat. No. 5,564,434 issued to Halperin et al. or an impedance sensor and associated sensor processing circuitry as described in U.S. Pat. No. 5,824,029 issued to Weijand et al., all incorporated herein by reference in their entireties, or may correspond to other types of physiologic sensors, as may be appropriate.

Figure 8:
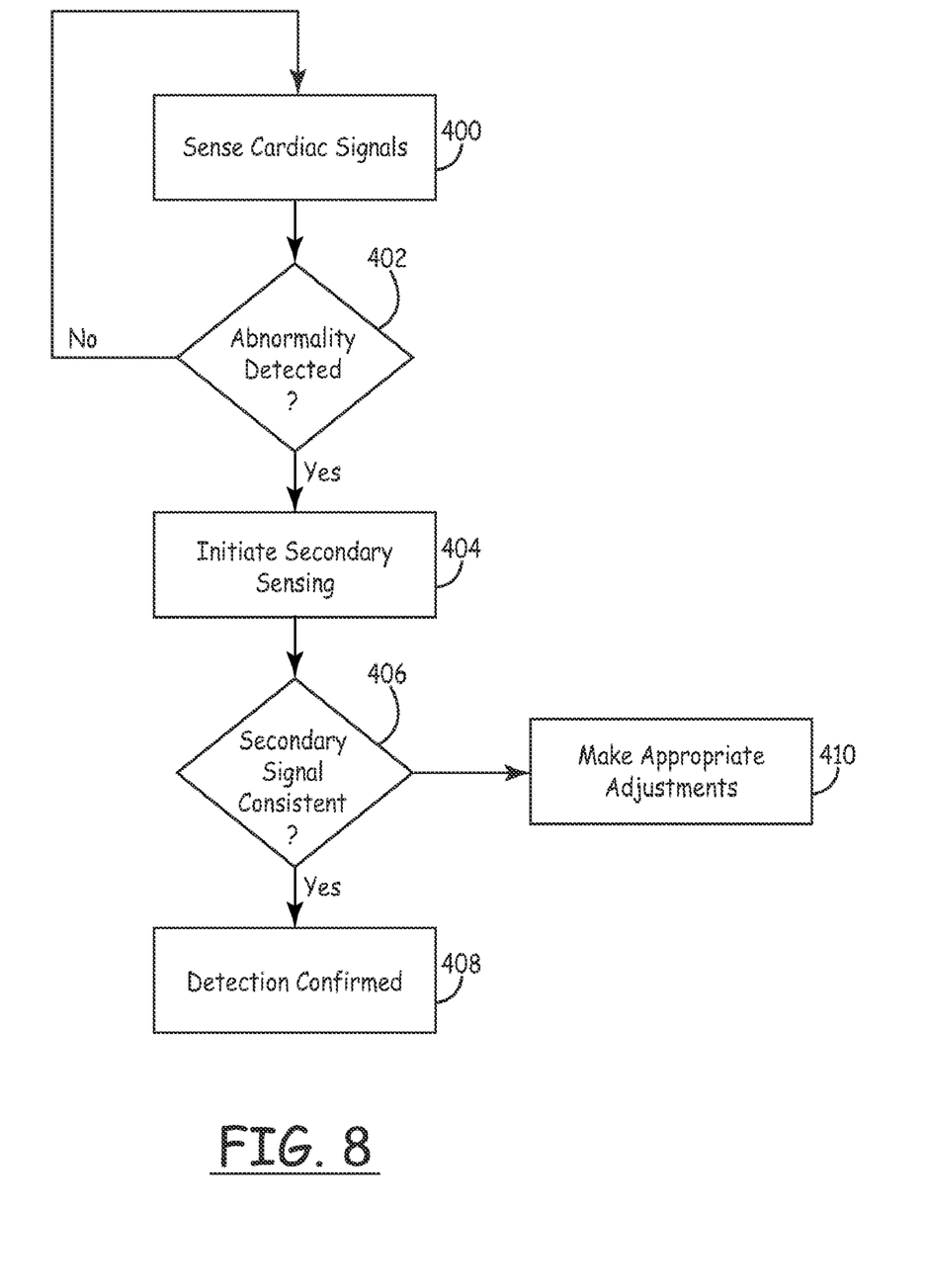
FIG. 8 is a flowchart of a method for detecting cardiac signals in a medical device according to an embodiment of the present invention.

FIG. 8 is a flowchart of a method for detecting cardiac signals in a medical device according to an embodiment of the present invention. As illustrated in FIG. 8, utilizing a medical device according to the present invention, such as those described above, for example, cardiac signals are sensed, Block 400, using appropriate electrodes associated with sensing. The sensed signals are used to generate an ECG signal and processed using known detection algorithms to determine whether an abnormality, such as a tachyarrhythmias is detected. Once an arrhythmia is detected using known arrhythmia detection algorithms, YES in Block 402, secondary sensing via the secondary sensor(s) is initiated, Block 404. Microprocessor 224 receives the signals detected by the one or more secondary sensors and determines whether the secondary signal is consistent with the detected abnormality, i.e., whether the secondary signal is indicative of an arrhythmia, Block 406. If the secondary signal is consistent with the detected abnormality, detection is confirmed, Block 408. If the secondary signal is not consistent with the detected abnormality, the likelihood that the detected arrhythmia was noise related or that oversensing has occurred increases, and therefore appropriate adjustments are made, Block 410.

In particular, according to an embodiment of the present invention, if the abnormality detected corresponds to a tachycardia event and the signals generated as a result of sensing by the secondary sensor or sensors during the same time period as the signals sensed by the ECG sensing electrodes are slow and/or regular compared with the ECG signal, the likelihood that the event is associated with oversensing on the ECG signal, rather than a tachycardia event, increases. Therefore additional analysis is needed and appropriate adjustments should be made. On the other hand, if the concomitant signals generated as a result of sensing by the secondary sensor or sensors are consistent with the signals sensed from the ECG sensing electrodes (e.g., have approximately the same timing as signals sensed by the ECG sensing electrodes), or if the secondary sensor indicates directly or indirectly a change in patient status, such as decreased patient activity, decreased hemodynamic output, or decreased local tissue perfusion, the identification of the tachycardia event is confirmed.

According to another embodiment of the present invention, if the abnormality detected by the ECG signal corresponds to a slow, asystolic event and the signals generated as a result of sensing by the secondary sensor or sensors during the same time period as the signals sensed by the ECG sensing electrodes are fast and indicative of a fast heart rate (e.g., for an acoustic sensor, an indication of fast heart rate with S1 heart sounds located approximately coincident with R-waves identified on the ECG signal), the likelihood that the detected event is associated with undersensing on the ECG signal, rather than a slow, asystolic event, increases. Therefore additional analysis is needed and appropriate adjustments should be made. Similarly, if the signals generated as a result of sensing by the secondary sensor or sensors during the same time period indicates directly or indirectly a change in patient status (e.g., decreased patient activity, decreased hemodynamic output, decreased local tissue perfusion), the likelihood of a tachycardia event needing intervention is increased, and additional analysis of the ECG and/or sensor signals is warranted to determine if and/or when therapy should be delivered. On the other hand, if the concomitant signals generated as a result of sensing by the secondary sensor or sensors are determined to corroborate the slow, asystolic rate measured by the ECG signal (e.g., an acoustic signal will have substantial heart sounds occurring with approximately the same timing as signals sensed by the ECG sensing electrodes), then the diagnosis of slow heart rate is confirmed.

Some of the techniques described above may be embodied as a computer-readable medium comprising instructions for a programmable processor such as a microprocessor. The programmable processor may include one or more individual processors, which may act independently or in concert. A "computer-readable medium" includes but is not limited to any type of computer memory such as floppy disks, conventional hard disks, CR-ROMS, Flash ROMS, nonvolatile ROMS, RAM and a magnetic or optical storage medium. The medium may include instructions for causing a processor to perform any of the features described above for initiating a session of the escape rate variation according to the present invention.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than as specifically described, without departing from the scope of the present invention. As to every element, it may be replaced by any one of infinite equivalent alternatives, only some of which are disclosed in the specification.

I claim:

1. A medical device, comprising:
   a first plurality of electrodes sensing cardiac signals and delivering therapy;
   a secondary sensor sensing the cardiac signals; and
   a microprocessor detecting a cardiac event in response to the sensing by the first plurality of electrodes, wherein the microprocessor generates a first sensed signal from cardiac signals sensed by the secondary sensor concomitant to the sensing by the first plurality of electrodes, compares the first sensed signal and the concomitantly sensed cardiac signals from the first plurality of electrodes, and determines whether the first sensed signal has one of a frequency less than signals associated with the concomitant sensing by the first plurality of electrodes and a regular beat pattern relative to the concomitant sensing by the first plurality of electrodes.

2. The device of claim 1, further comprising a device housing capable of being subcutaneously positioned within a patient, the microprocessor being positioned within the device housing, wherein the first plurality of electrodes and the secondary sensor are positioned along the device housing.

3. The device of claim 1, further comprising:
   a device housing capable of being subcutaneously positioned within a patient, the microprocessor being positioned within the device housing; and
   a lead body extending from the device housing, wherein the first plurality of electrodes are positioned along the lead body and the secondary sensor is positioned along the device housing.

4. The device of claim 3, wherein the lead body is capable of being subcutaneously positioned within the patient.

5. The device of claim 1, wherein the secondary sensor comprises an acoustic sensor.

6. The device of claim 1, further comprising:
   a device housing capable of being subcutaneously positioned within a patient, the microprocessor being positioned within the device housing;
   a header block positioned on the device housing; and
   a lead body extending from the header block and capable of being subcutaneously positioned within the patient, wherein the first plurality of electrodes are positioned along one of the device housing and the lead body and the secondary sensor is positioned along the header block.

7. The device of claim 1, further comprising:
   a device housing capable of being subcutaneously positioned within a patient, the microprocessor being positioned within the device housing;
   a header block positioned on the device housing;
   a first lead body extending from the header block; and
   a second lead body extending from the header block, wherein the first plurality of electrodes are positioned along one of the device housing and the first lead body and the secondary sensor is positioned along one of the header block and the second lead body.

8. The device of claim 1, further comprising:
   control circuitry controlling output from the first plurality of electrodes and the second plurality of electrodes, wherein the control circuitry initiates sensing of the cardiac signals by the secondary sensor in response to the microprocessor detecting the cardiac event.

9. The device of claim 1, wherein the microprocessor determines whether a timing of the first sensed signal is approximately equal to signals associated with the sensing by the first plurality of electrodes and determines whether the first sensed signal indicates a change in patient status.

10. The device of claim 9, wherein the change in patient status corresponds to one of decreased patient activity, decreased hemodynamic output, and decreased local tissue perfusion.

11. The device of claim 1, wherein the microprocessors determines the cardiac signals sensed by the first plurality of electrodes are associated with oversensing in response to the cardiac signals sensed by the first plurality of electrodes being determined to be a tachycardia event and the concurrently sensed cardiac signals from the secondary sensor being one of slow and regular compared to the cardiac signals sensed by the first plurality of electrodes.

12. The device of claim 1, wherein the microprocessor determines the cardiac signals sensed by the first plurality of electrodes are associated with undersensing in response to the cardiac signals sensed by the first plurality of electrodes corresponding to a slow, asystolic event and the concurrently sensed cardiac signals from the secondary sensor being fast and indicative of a fast heart rate.

13. A method of detecting cardiac signals, comprising:
   sensing cardiac signals via a first plurality of electrodes to generate a sensed signal;
   determining whether the sensed signal corresponds to a cardiac event;
   sensing the cardiac signals via a second plurality of electrodes; and
   generating a first sensed signal from cardiac signals sensed by the second plurality of electrodes concomitant to the sensing by the first plurality of electrodes, comparing the first sensed signal and the concomitantly sensed cardiac signals from the first plurality of electrodes, and determining whether the first sensed signal has one of a frequency less than signals associated with the concomitant sensing by the first plurality of electrodes and a regular beat pattern relative to the concomitant sensing by the first plurality of electrodes.

14. The method of claim 13, wherein the first plurality of electrodes and the second plurality of electrodes are positioned along a device housing capable of being subcutaneously implanted within a patient.

15. The method of claim 13, wherein the second plurality of electrodes are positioned along a device housing capable of being subcutaneously positioned within a patient and the first plurality of electrodes are positioned along a lead body extending from the device housing.

16. The method of claim 15, wherein the lead body is capable of being subcutaneously positioned within the patient.

17. The method of claim 13, wherein the second plurality of electrodes include an acoustic sensor.

18. The method of claim 13, wherein the first plurality of electrodes are positioned along one of a device housing capable of being subcutaneously positioned within a patient and a lead body extending from a header block positioned on the device housing, and the second plurality of electrodes are positioned along the header block.

19. The method of claim 13, wherein the first plurality of electrodes are positioned along one of a device housing capable of being subcutaneously positioned within a patient and a first lead body extending from a header block positioned on the device housing, and the second plurality of electrodes are positioned along one of the header block and a second lead body extending from the header block.

20. The method of claim 13, further comprising:
determining whether a timing of the first sensed signal is approximately equal to signals associated with the sensing by the first plurality of electrodes; and
determining whether the first sensed signal indicates a change in patient status.

21. The method of claim 20, wherein the change in patient status corresponds to one of decreased patient activity, decreased hemodynamic output, and decreased local tissue perfusion.

22. A medical device, comprising;
an electrode for sensing cardiac signals;
an acoustic sensor for sensing heart sounds associated with the cardiac signals; and
a microprocessor for comparing sensed heart sounds to cardiac signals sensed concurrently with the sensed heart sounds and determining the likelihood that one of oversensing and undersensing is occurring on the sensed cardiac signals in response to the comparing.

23. The device of claim 22, wherein the microprocessors determines the cardiac signals sensed by the electrode are associated with oversensing in response to the sensed cardiac signals being determined to be a tachycardia event and the concurrently sensed heart sounds being one of slow and regular compared to the cardiac signals sensed by the electrode.

24. The device of claim 22, wherein the microprocessor determines the cardiac signals sensed by the electrode are associated with undersensing in response to the sensed cardiac signals corresponding to a slow, asystolic event and the concurrently sensed heart sounds being fast and indicative of a fast heart rate.

* * * * *